(12) United States Patent
Hegg et al.

(10) Patent No.: US 9,101,678 B2
(45) Date of Patent: Aug. 11, 2015

(54) HEAT-SANITIZATION OF SURFACES

(75) Inventors: Michael C. Hegg, Seattle, WA (US);
David R. Nash, Arlington, WA (US);
Benjamin K. Wilson, Kirkland, WA (US)

(73) Assignee: Elwha LLC, Bellevue, WA (US)

(*) Notice: Subject to any disclaimer, the term of this patent is extended or adjusted under 35 U.S.C. 154(b) by 736 days.

(21) Appl. No.: 13/373,138

(22) Filed: Nov. 3, 2011

(65) Prior Publication Data
US 2013/0115131 A1 May 9, 2013

(51) Int. Cl.
*A61L 2/08* (2006.01)
*A61L 2/24* (2006.01)
*A61L 2/28* (2006.01)

(52) U.S. Cl.
CPC ... *A61L 2/08* (2013.01); *A61L 2/24* (2013.01); *A61L 2/085* (2013.01); *A61L 2/28* (2013.01); *A61L 2202/11* (2013.01)

(58) Field of Classification Search
CPC .............. A61L 2/08; A61L 2/24; A61L 2/28; A61L 2/085; A61L 2202/11
USPC ...................................................... 422/82.11
See application file for complete search history.

(56) References Cited

U.S. PATENT DOCUMENTS

| | | |
|---|---|---|
| 2,602,724 A | 7/1952 | Batchelor |
| 3,437,777 A * | 4/1969 | Chiba et al. .................... 219/750 |
| 4,296,068 A | 10/1981 | Hoshino |
| 4,598,579 A | 7/1986 | Cummings et al. |
| 4,788,975 A | 12/1988 | Shturman et al. |
| 5,000,731 A | 3/1991 | Wong et al. |
| 5,127,735 A | 7/1992 | Pitt |
| 5,155,707 A | 10/1992 | Fisher |
| 5,156,839 A | 10/1992 | Pennell et al. |
| 5,164,164 A | 11/1992 | Strickler et al. |
| 5,326,567 A | 7/1994 | Capelli |
| 5,367,720 A | 11/1994 | Stephens et al. |
| 5,538,691 A * | 7/1996 | Tosa et al. ...................... 356/246 |
| 5,544,268 A * | 8/1996 | Bischel et al. .................... 385/4 |
| 5,607,683 A | 3/1997 | Capelli |
| 5,622,848 A | 4/1997 | Morrow |
| 5,630,379 A | 5/1997 | Gerk et al. |
| 5,704,352 A | 1/1998 | Tremblay et al. |
| 5,733,270 A | 3/1998 | Ling et al. |

(Continued)

FOREIGN PATENT DOCUMENTS

| | | |
|---|---|---|
| WO | WO 91/06855 A2 | 5/1991 |
| WO | WO/92/01222 | 1/1992 |

(Continued)

OTHER PUBLICATIONS

Albert, Richard K. and Condie, Frances; "Medical Intelligence: Hand-Washing Patterns in Medical Instensive-Care Units"; New England Journal of Medicine; Jun. 1981; pp. 1465-1466; vol. 304, No. 24.

(Continued)

*Primary Examiner* — Regina M Yoo
(74) *Attorney, Agent, or Firm* — Advent, LLP

(57) ABSTRACT

Solutions for limiting the undesirable spread of pathogens by indirect contact are provided. The solutions involve heat-sanitization of contact regions on articles or fixtures by flowing selected electromagnetic radiation energy through underlying waveguide structures substantially parallel to the contact regions.

16 Claims, 6 Drawing Sheets

(56) References Cited

U.S. PATENT DOCUMENTS

| | | |
|---|---|---|
| 5,771,528 A | 6/1998 | Nappi, Sr. |
| 5,820,821 A | 10/1998 | Kawagoe et al. |
| 5,838,015 A * | 11/1998 | Burdick et al. ............ 250/504 R |
| 5,993,382 A | 11/1999 | Pruitt, Sr. |
| 6,135,990 A | 10/2000 | Heller et al. |
| 6,141,465 A * | 10/2000 | Bischel et al. .................... 385/4 |
| 6,143,035 A | 11/2000 | McDowell |
| 6,280,604 B1 | 8/2001 | Allen et al. |
| 6,304,786 B1 | 10/2001 | Heil, Jr. et al. |
| 6,348,042 B1 | 2/2002 | Warren, Jr. |
| 6,350,263 B1 | 2/2002 | Wetzig et al. |
| 6,418,342 B1 | 7/2002 | Owen et al. |
| 6,426,066 B1 | 7/2002 | Najafi et al. |
| 6,440,097 B1 | 8/2002 | Kupiecki |
| 6,443,147 B1 | 9/2002 | Matter |
| 6,451,003 B1 | 9/2002 | Prosl et al. |
| 6,461,569 B1 | 10/2002 | Boudreaux |
| 6,478,778 B1 | 11/2002 | Jacobsen et al. |
| 6,488,704 B1 | 12/2002 | Connelly et al. |
| 6,506,416 B1 | 1/2003 | Okauchi et al. |
| 6,585,677 B2 | 7/2003 | Cowan, Jr. et al. |
| 6,663,297 B1 * | 12/2003 | Goldstein ........................ 385/97 |
| 6,730,113 B2 | 5/2004 | Eckhardt et al. |
| 6,743,190 B2 | 6/2004 | Connelly et al. |
| 6,750,055 B1 | 6/2004 | Connelly et al. |
| 6,789,183 B1 | 9/2004 | Smith et al. |
| 6,793,642 B2 | 9/2004 | Connelly et al. |
| 6,802,811 B1 | 10/2004 | Slepian |
| 6,831,748 B2 | 12/2004 | Tittel et al. |
| 6,913,589 B2 | 7/2005 | Dextradeur et al. |
| 6,914,279 B2 | 7/2005 | Lu et al. |
| 6,932,787 B2 | 8/2005 | Cowan et al. |
| 6,960,201 B2 | 11/2005 | Cumbie |
| 6,980,716 B1 | 12/2005 | Diaz et al. |
| 7,118,548 B2 | 10/2006 | Børgesen |
| 7,143,709 B2 | 12/2006 | Brennan et al. |
| 7,151,139 B2 | 12/2006 | Tiller et al. |
| 7,160,931 B2 | 1/2007 | Cheng et al. |
| 7,183,048 B2 | 2/2007 | Felkner et al. |
| 7,195,608 B2 | 3/2007 | Burnett |
| 7,217,425 B2 | 5/2007 | Serhan et al. |
| 7,226,441 B2 | 6/2007 | Kulessa |
| 7,232,429 B2 | 6/2007 | Moreci |
| 7,236,821 B2 | 6/2007 | Cates et al. |
| 7,238,363 B2 | 7/2007 | Mansouri et al. |
| 7,244,232 B2 | 7/2007 | Connelly et al. |
| 7,253,152 B2 | 8/2007 | Panero et al. |
| 7,276,255 B2 | 10/2007 | Selkon |
| 7,288,232 B2 | 10/2007 | Morrow et al. |
| 7,306,620 B2 | 12/2007 | Cumbie |
| 7,309,330 B2 | 12/2007 | Bertrand et al. |
| 7,334,594 B2 | 2/2008 | Ludin |
| 7,345,372 B2 | 3/2008 | Roberts et al. |
| 7,348,021 B2 | 3/2008 | Klein |
| 7,354,575 B2 | 4/2008 | Shachar et al. |
| 7,390,310 B2 | 6/2008 | McCusker et al. |
| 7,396,676 B2 | 7/2008 | Robotti et al. |
| 7,442,372 B2 | 10/2008 | Kakkis |
| 7,524,298 B2 | 4/2009 | Gharib et al. |
| 7,535,692 B2 | 5/2009 | Krupenkin et al. |
| 7,570,018 B2 | 8/2009 | Waguespack |
| 7,667,200 B1 * | 2/2010 | Watts et al. ................ 250/338.1 |
| 2002/0182262 A1 | 12/2002 | Selkon |
| 2003/0017073 A1 | 1/2003 | Eckhardt et al. |
| 2003/0109907 A1 | 6/2003 | Shadduck |
| 2003/0225331 A1 | 12/2003 | Diederich et al. |
| 2004/0022669 A1 | 2/2004 | Ruan et al. |
| 2004/0098055 A1 | 5/2004 | Kroll et al. |
| 2004/0149582 A1 | 8/2004 | Kovacs |
| 2004/0208940 A1 | 10/2004 | Selkon |
| 2004/0253138 A1 | 12/2004 | Malak |
| 2005/0142157 A1 | 6/2005 | Alimi |
| 2005/0164169 A1 | 7/2005 | Malak |
| 2005/0203495 A1 | 9/2005 | Malak |
| 2005/0245557 A1 | 11/2005 | Schoenhard et al. |
| 2005/0288654 A1 | 12/2005 | Nieman et al. |
| 2006/0004317 A1 | 1/2006 | Mauge et al. |
| 2006/0020239 A1 | 1/2006 | Geiger et al. |
| 2006/0122543 A1 | 6/2006 | Mayer et al. |
| 2006/0210602 A1 | 9/2006 | Sehl et al. |
| 2006/0287660 A1 | 12/2006 | Syed et al. |
| 2007/0031777 A1 | 2/2007 | Wang et al. |
| 2007/0074672 A1 | 4/2007 | Torgerson et al. |
| 2007/0142874 A1 | 6/2007 | John |
| 2007/0156039 A1 | 7/2007 | Casciani et al. |
| 2007/0173755 A1 | 7/2007 | Alimi et al. |
| 2007/0176117 A1 | 8/2007 | Redmond et al. |
| 2007/0196357 A1 | 8/2007 | Alimi et al. |
| 2007/0207073 A1 | 9/2007 | Drucker |
| 2007/0225800 A1 | 9/2007 | Sahatjian et al. |
| 2007/0249969 A1 | 10/2007 | Shields, Jr. |
| 2007/0274909 A1 | 11/2007 | Justel et al. |
| 2007/0276208 A1 | 11/2007 | Connelly et al. |
| 2008/0033519 A1 | 2/2008 | Burwell et al. |
| 2008/0039768 A1 | 2/2008 | Francis |
| 2008/0051691 A1 | 2/2008 | Dragoon et al. |
| 2008/0051736 A1 | 2/2008 | Rioux et al. |
| 2008/0056933 A1 | 3/2008 | Moore et al. |
| 2008/0058798 A1 | 3/2008 | Wallace et al. |
| 2008/0064980 A1 | 3/2008 | Lee et al. |
| 2008/0095977 A1 | 4/2008 | Aizenberg et al. |
| 2008/0118546 A1 | 5/2008 | Thatcher et al. |
| 2008/0223717 A1 | 9/2008 | Isaksson et al. |
| 2008/0234786 A1 | 9/2008 | Cumbie |
| 2008/0248993 A1 | 10/2008 | Hannappel et al. |
| 2008/0253712 A1 | 10/2008 | Allen et al. |
| 2008/0265179 A1 | 10/2008 | Havens et al. |
| 2009/0054824 A1 | 2/2009 | Melsheimer et al. |
| 2009/0054827 A1 | 2/2009 | Eide |
| 2009/0110711 A1 | 4/2009 | Trollsas et al. |
| 2009/0118661 A1 | 5/2009 | Moehle et al. |
| 2009/0185988 A1 | 7/2009 | Maleski et al. |
| 2009/0306478 A1 * | 12/2009 | Mizuyoshi .................... 600/178 |
| 2010/0272386 A1 * | 10/2010 | Fu et al. ......................... 385/14 |
| 2012/0169674 A1 * | 7/2012 | Sekiya ......................... 345/179 |

FOREIGN PATENT DOCUMENTS

| | | |
|---|---|---|
| WO | WO/97/00586 | 1/1997 |
| WO | WO/00/09733 | 2/2000 |
| WO | WO/00/29613 | 5/2000 |
| WO | WO/00/56185 | 9/2000 |
| WO | WO/01/13926 A2 | 3/2001 |
| WO | WO/01/54704 A1 | 8/2001 |
| WO | WO/02/102421 A1 | 12/2002 |
| WO | WO/2004/027116 A2 | 4/2004 |
| WO | WO/2004/031077 A2 | 4/2004 |
| WO | WO/2005/100100 A1 | 10/2005 |
| WO | WO/2005/117914 A2 | 12/2005 |
| WO | WO/2006/044324 A2 | 4/2006 |
| WO | WO/2007/070801 A3 | 6/2007 |
| WO | WO/2007/085021 A3 | 7/2007 |
| WO | WO/2008/020770 A1 | 2/2008 |
| WO | WO/2008/073774 A1 | 6/2008 |
| WO | WO/2008/083390 A2 | 10/2008 |
| WO | WO 2011033913 A1 * | 3/2011 .............. G06F 3/042 |

OTHER PUBLICATIONS

Bozhevolnyi, Sergey I. et al.; "Photonic bandgap structures for long-range surface plasmon polaritons"; Optics Communications; bearing a date of 2005; pp. 328-333; vol. 250; Elsevier B.V.
ESR European Search Report; European App. No. EP 08 25 1153; Dec. 15, 2008; p. 1.
European Search Report; European App. No. EP 08 25 1153; Jul. 10, 2009; pp. 1-2.
PCT International Search Report; International App. No. PCT/US09/06393; May 13, 2010; pp. 1-4.
PCT International Search Report; International App. No. PCT/US10/00579; May 3, 2010; pp. 1-2.
PCT International Search Report; International App. No. PCT/US 09/04028; Sep. 10, 2009; pp. 1-2.
U.S. Appl. No. 11/973,010, Hyde et al.

(56) References Cited

OTHER PUBLICATIONS

Aarabi, Shahram et al.; "Research in Translation: Hypertrophic Scar Formation Following Burns and Trauma: New Approaches to Treatment"; PLoS Medicine; Sep. 2007; pp. 1464-1470; vol. 4, Issue 9, No. e234; located at: www.plosmedicine.org.

Abdollahi, Amir; "Apoptosis Signals in Lymphoblasts Induced by Focused Ultrasound"; The FASEB Journal-FJ Express; Sep. 2004; pp. 1413-1414; vol. 18; FASEB.

"Arglaes® Controlled-Release Silver Technology"; Medicine; 2003; 6 pages; Medline Industries, Inc.; located at: www.medline.com.

Ashush, Hagit et al.; "Apoptosis Induction of Human Myeloid Leukemic Cells by Ultrasound Exposure"; Cancer Research; bearing a date of Feb. 15, 2000; pp. 1014-1020; vol. 60.

Bozhevolnyi, Sergey I. et al.; "Photonic bandgap structures for long-range sruface plasmon polaritons"; Optics Communications; bearing a date of 2005; pp. 328-333; vol. 250; Elsevier B.V.

Brogden, Kim A.; "Antimicrobial Peptides: Pore Formers or Metabolic Inhibitors in Bacteria?"; Nature Reviews, Microbiology; Mar. 2005; pp. 238-250; vol. 3.

Carcillo, Joseph A. et al.; "Early Markers of Infection and Sepsis in Newborns and Children"; Leading Articles, Advances in Sepsis; 2006; pp. 118-125; vol. 5, No. 4.

Caricchio, Roberto et al.; "Ultraviolet B Radiation-Induced Cell Death: Critical Role of Ultraviolet Dose in Inflammation and Lupus Autoantigen Redistribution"; The Journal of Immunology; 2003; pp. 5778-5786; vol. 171; The American Association of Immunlogists, Inc.

Chen, Ting-Hsuan et al.; "A Wettability Switchable Surface Driven by Electrostatic Induced Surface Morphology Change Without Energy Interference on Reagents in Droplets"; MEMS; Jan. 2006; pp. 178-181; IEEE.

Chang, Gang et al.; "Switchable Polymer Surfaces: A Switchable Biocompatible Polymer Surface with Self-Sterilizing and Nonfouling Capabilities"; Angewandte Chemie; 2008; pp. 8831-8834; vol. 47; Wiley-VCH Verlag GmbH & Co.

De Fabo, Edward C.; "Advances in Brief: Ultraviolet B but not Ultraviolet A Radiation Initiates Melanoma"; Cancer Research; bearing a date of Sep. 15, 2004; pp. 6372-6376; vol. 64; American Association for Cancer Research.

Donlan, R. M. et al.; "Model Systems for Growing and Quantifying *Streptococcus Pneumoniae* Biofilms In Situ and in Real Time"; Applied and Environmental Microbiology; Aug. 2004; pp. 4980-4988; vol. 70, No. 8; American Society for Microbiology.

"Fact Sheet: Cerebrospinal Fluid Shunt Systems for the Management of Hydrocephalus"; Hydrocephalus Association; 2000; 7 pages; Hydrocephalus Association; located at: www.hydroassoc.org.

Feng, Xinjian et al.; "Reversible Super-Hydrophobicity to Super-Hydrophilicity Transition of Aligned ZnO Nanorod Films"; JACS Communications; 2004; pp. 62-63; vol. 126; American Chemical Society.

Feng, Yi et al.; "Gastric Cancer: Low Intensity Ultrasound-Induced Apoptosis in Human Gastric Carcinoma Cells"; World Journal of Gastroenterology; bearing a date of Aug. 21, 2008; pp. 4873-4879; vol. 14, No. 31; The WJG Press; located at: www.wjgnet.com.

Fogh-Andersen, Niels et al.; "Composition of Interstitial Fluid"; General Clinical Chemistry; 1995; pp. 1522-1525; vol. 41, No. 10.

Forbes, Peter; "Scientific American: Self-Cleaning Materials: Lotus Leaf-Inspired Nanotechnology"; Scientific American Magazine; bearing a date of Jul. 30, 2008; pp. 1-5; printed on Nov. 21, 2008.

Goclawski, Jaroslaw et al.; "The Measurement of Wetting Angle by Applying and ADSA Model of Sessile Drop on Selected Textile Surfaces"; Fibres and Textiles in Eastern Europe; Apr./Jun. 2008; pp. 84-88; vol. 16, No. 2(67).

Grunfeld, Carl; "Lipids, Lipoproteins, Triglyceride Clearance, and Cytokines in Human Immunodeficiency Virus Infection and the Acquired Immunodeficiency Syndrome"; Journal of Clinical Endocrinology and Metabolism; 1992; pp. 1045-1052; vol. 74, No. 5; The Endocrine Society.

Imam, S.K. et al.; "Radiotracers for Imaging of Infection and Inflammation- A Review"; World Journal Nuclear Medicine.; Jan. 2006; pp. 40-55; vol. 5, No. 1.

Killer, H. E. et al.; "The Optic Nerve: A New Window into Cerebrospinal Fluid Composition?"; Brain; 2006; pp. 1027-1030; vol. 129.

Lahann, Joerg; "A Reversibly Switching Surface"; Reports, Science; bearing a date of Jan. 17, 2003; pp. 371-374 (plus Erratum); vol. 299; located at: www.sciencemag.org.

Lepock, James R.; "Cellular Effects of Hyperthermia: Relevance to the Minimum Dose for Thermal Damage"; International Journal of Hyperthermia, Taylor & Francis healthsciences; May-Jun. 2003; pp. 252-266; vol. 19, No. 3; Taylor & Francis Ltd.

Lin, Yi-Hsin; "Electrically Tunable Wettability of Liquid Crystal/Polymer Composite Films"; Optics Express; bearing a date of Oct. 27, 2008; pp. 17591-17598; vol. 16, No. 22; OSA.

Masteikova, Ruta et al.; "Stimuli-Sensitive Hydrogels in Controlled and Sustained Drug Delivery"; Medicina; 2003; pp. 19-24; vol. 39, No. 2.

McKenna, Susan M. et al.; "The Inhibition of Bacterial Growth by Hypochlorous Acid"; Biochemistry; 1988; pp. 685-692; vol. 254.

Nejat, Farideh et al.; "Original Article: A Randomized Trial of Ceftriaxone Versus Trimethoprimsulfamethoxazole to Prevent Ventriculoperitoneal Shunt Infection"; Journal of Microbiology, Immunology and Infection; 2008; pp. 112-117; vol. 41; Journal of Microbiology, Immunology and Infection.

NG, P C; "Review: Diagnostic Markers of Infection in Neonates"; Arch Dis Child Fetal Neonatal Ed; 2004; pp. F229-F235; vol. 89; located at: www.archdischild.com.

Okada, Ayako et al.; "Inhibition of Biofilm Formation Using Newly Developed Coating Materials with Self-Cleaning Properties"; Dental Materials Journal; 2008; pp. 565-572; vol. 27, No. 4.

Rathmell, James P. et al.; "Infectious Risks of Chronic Pain Treatments: Injection Therapy, Surgical Implants, and Intradiscal Techniques"; Regional Anesthesia and Pain Medicine; 2006; pp. 346-352; vol. 31, No. 4.

Rediske, Andrea M. et al.; "Pulsed Ultrasound Enhances the Killing of *Escherichia coli* Biofilms by Aminoglycoside Antibiotics In Vivo"; Antimicrobial Agents and Chemotherapy; Mar. 2000; pp. 771-772; vol. 44, No. 3; American Society for Microbiology; downloaded on Aug. 24, 2009.

Reid, Marvin et al.; "The Acute-Phase Protein Response to Infection in Edematous and Nonedematous Protein-Energy Malnutrition"; The American Journal of Clinical Nutrition; 2002; pp. 1409-1415; vol. 76; American Society for Clinical Nutrition.

Roti Roti, Joseph L.; "Review: Cellular Responses to Hyperthermia (40-46° C.): Cell Killing and Molecular Events"; Informa healthcare; Feb. 2008; pp. 3-15; vol. 24, No. 1; Informa UK Ltd.

Seehusen, Dean A. et al.; "Cerebrospinal Fluid Analysis"; American Family Physician; bearing a date of Sep. 15, 2003; pp. 1103-1108; vol. 68, No. 6; located at: www.aafg.org/afp.

Setroikromo, R.; "Heat Shock Proteins and Bcl-2 Expression and Function in Relation to the Differential Hyperthermic Sensitivity between Leukemic and Normal Hematopoietic Cells"; Cell Stress & Chaperones; 2007; pp. 320-330; vol. 12, No. 4; Cell Stress Society International.

"SilvaSorb® Targeted Antimicrobial Protection"; Medline; 2005; 16 pages; Medline Industries Inc.; located at www.medline.com.

Sodja, Caroline; "Splenic T Lymphocytes Die Preferentially During Heat-Induced Apoptosis: NuMA Reorganization as a Marker"; Journal of Cell Science; 1998; pp. 2305-2313; vol. 111; The Company of Biologists Limited.

Stankiewicz, Adam R.; "Hsp70 Inhibits Heat-Induced Apoptosis Upstream of Mitochondria by Preventing Bax Translocation"; The Journal of Biological Chemistry; Bearing a date of Nov. 18, 2005; pp. 38729-38739; vol. 280, No. 46; The American Society for Biochemistry and Molecular Biology, Inc.

(56) References Cited

OTHER PUBLICATIONS

Tuteja, Anish et al.; "Robust Omniphobic Surfaces"; PNAS; bearing a date of Nov. 25, 2008; pp. 18200-18205; vol. 105, No. 47; The National Academy of Sciences of the USA.

Wang, Shutao; "Review: Photoresponsive Surfaces with Controllable Wettability"; Journal of Photochemistry and Photobiology C: Photochemistry Review, Science Direct; 2007; pp. 18-29; vol. 8; Elsevier B.V.

Wang, Zhe et al.; "APD: The Antimicrobial Peptide Database"; Nucleic Acids Research; 2004; pp. D590-D592; vol. 32; Oxford University Press.

Watson, Mark A.; "Review: Clinical Utility of Biochemical Analysis of Cerebrospinal Fluid"; Clinical Chemistry; 1995; pp. 343-360; vol. 41, No. 3.

Wentworth, Jr., Paul et al.; "Reports: Evidence for Antibody-Catalyzed Ozone Formation in Bacterial Killing and Inflammation"; Science AAAS; 2002; pp. 2195-2199; vol. 298; downloaded on Jul. 14, 2009; located at: www.sciencemag.org.

Zhong, Yinghui et al.; "Review: Biomaterials for the Central Nervous System"; Journal of the Royal Society Interface; 2008; pp. 957-975; vol. 5; The Royal Society.

\* cited by examiner

| 410
providing a selected electromagnetic radiation absorber portion in the outer surface region; and |
|---|
| 420
flowing selected electromagnetic radiation energy through an underlying waveguide structure substantially parallel to the outer surface region so that the selected electromagnetic radiation absorber portion is coupled to and heated by the electromagnetic radiation energy flow to a positive temperature that heat-sanitizes an exposed portion of the outer surface region. |

HEAT-SANITIZATION OF SURFACES

BACKGROUND

Diseases and infections can be transmitted by indirect contact. Any contact surface, which is touched by more than one person, can be a transfer point for harmful germs spreading diseases and infections through a population. An example is the common cold. A person, who has a cold, can leave cold virus behind on a door handle he or she touches. A non-infected person, who later touches the door handle, can pick up the cold virus from the door handle and catch the same cold.

For certain high risk environments (e.g., restrooms, food service and health care facilities), public health programs recommend hand washing or hand rubbing routines for maintaining good hand hygiene to prevent or reduce propagation of communicable diseases and infections. However, time and facilities constraints present are major obstacles to maintaining good hand hygiene. Many studies of nosocomial infections show that hand washing protocols are not properly followed even by health care providers. General compliance rates of health care providers with hospital-recommended hand washing or hand rubbing protocols are low. The poor compliance rates have been attributed in part to a lack of knowledge of when and how to clean or disinfect hands, and in part to time constraints and poor access to hand washing facilities or hand rubbing products. (See e.g., Albert R. K., Condie F., NEJM 1981; 304(24):1465-6).

The time and facilities constraints that impede good hand hygiene in hospital environments are even more severe obstacles for achieving good hand hygiene in other public environments. For example, it is not practical to provide hand washing facilities at every touch screen in an airport, or at ATM or contact surface in a bank. Further, even where hand washing facilities are provided (e.g., in restrooms), hand washing can be counterproductive. A person, after washing hands, could pick up germs by turning a water faucet handle off, or touching a restroom exit door handle.

Consideration is now being given to other solutions for limiting the undesirable spread of pathogens by indirect contact. Some such solutions may avoid, for example, the time and facilities constraints that hinder solutions that rely on voluntary hand washing by individuals.

SUMMARY

Approaches to limiting the spread of pathogens, for example, by indirect contact are provided.

The foregoing summary is illustrative only and is not intended to be limiting. In addition to the illustrative aspects, embodiments, and features described above, further aspects, embodiments, and features of the solutions will become apparent by reference to the drawings and the following detailed description.

BRIEF DESCRIPTION OF THE FIGURES

In the accompanying drawings:

FIG. 4 is a flow diagram of an exemplary method for heat-sanitizing article surfaces, in accordance with the principles of the solutions described herein.

Throughout the figures, unless otherwise stated, the same reference numerals and characters are used to denote like features, elements, components, or portions of the illustrated embodiments.

DESCRIPTION

In the following description of exemplary embodiments, reference is made to the accompanying drawings, which form a part hereof. It will be understood that embodiments described herein are exemplary, but are not meant to be limiting. Further, it will be appreciated that the solutions described herein can be practiced or implemented by other than the described embodiments. Modified embodiments or alternate embodiments may be utilized, in the spirit and scope of the solutions described herein.

Sterilization, disinfection, and sanitization of an object are terms that may have specific meanings corresponding to various degrees of control of microbial growth. Sterilization of a surface may, for example, refer to killing of all microbial growth on the surface. Disinfection of a surface may refer to reducing the number of viable microorganisms on the surface, and sanitization may refer to cleaning the surface to reduce or remove a number of the microorganisms. However, for convenience in description, a single term "sanitization" may be used herein to describe any degree of control of microbial growth including, for example, any killing or reduction of viable microbial growth that may be otherwise described by the terms sterilization or disinfection.

Sanitization of a surface, in general, requires application of suitable chemical or physical antimicrobial agents to the surface to kill, impair or remove the microbes. Exemplary chemical antimicrobial agents include surfactants, various organic acids and bases, heavy metals, halogen-containing compounds, alcohols, phenol and phenolics, oxidizing agents, alkylating agents, dyes, etc. Exemplary physical antimicrobial agents include heat, ultraviolet radiation, ultrasonic waves, etc.

The sanitization agents are usually applied externally to the surfaces periodically or in between use of the surfaces. In many cases, the surfaces (e.g., touch screens, key boards, etc.) are in continuous use or must be continuously available for use. Sanitization of such surfaces by application of external physical or chemical agents may require interruption of the surfaces availability for use. In contrast, the sanitization techniques and solutions described herein may be used to sanitize surfaces without interrupting their use or availability.

Figure 1:
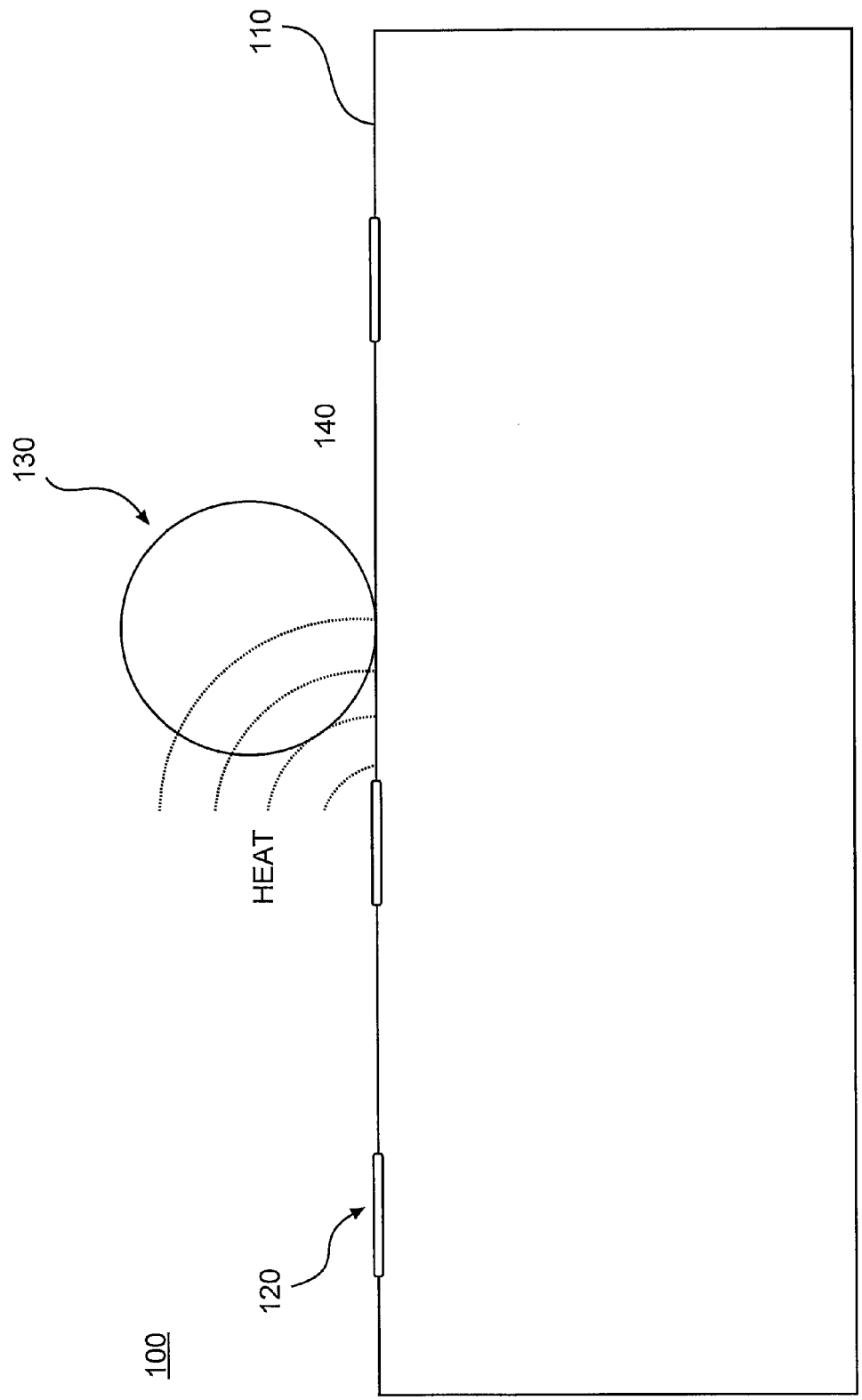
FIG. 1 is a schematic illustration of an exemplary article having a contact surface that can be heat-sanitized to kill, impair or remove microbial growth, in accordance with the principles of the solutions described herein.

In one approach, surface sanitization may be achieved by localized heating of surface portions to destroy or impair pathogens or other organic life forms. FIG. 1 shows, for example, an article 100 with an exterior surface 110 which includes a heat-radiating or re-radiating portion 120. Heat, which is radiated from portion 120, may be intense enough to kill or impair a microorganism 130 in local region 140. In accordance with the principles of the solutions described herein, energy for reradiation as heat is delivered to the heat-radiating portion 120 for heat-sanitization in a manner that does not significantly interfere with use or operation of surface 110 or article 100.

In one approach, energy is delivered to the heat-radiating portions of the surface in the form of electromagnetic energy. The electromagnetic energy may be delivered specifically to the heat-radiating portions via a suitable wave guide structure. The heat-radiating portions of the surfaces may, for example, directly or indirectly absorb energy propagating through the suitable wave guide structure and reradiate such absorbed energy as heat.

The heat-radiating portions of the surfaces (e.g., surface portions 120) may also be referred to herein interchangeably as heat- or energy-absorbing portions as appropriate in the context of the description of the functions of such portions (i.e., absorbing energy or re-radiating such energy as heat).

Figure 2A:
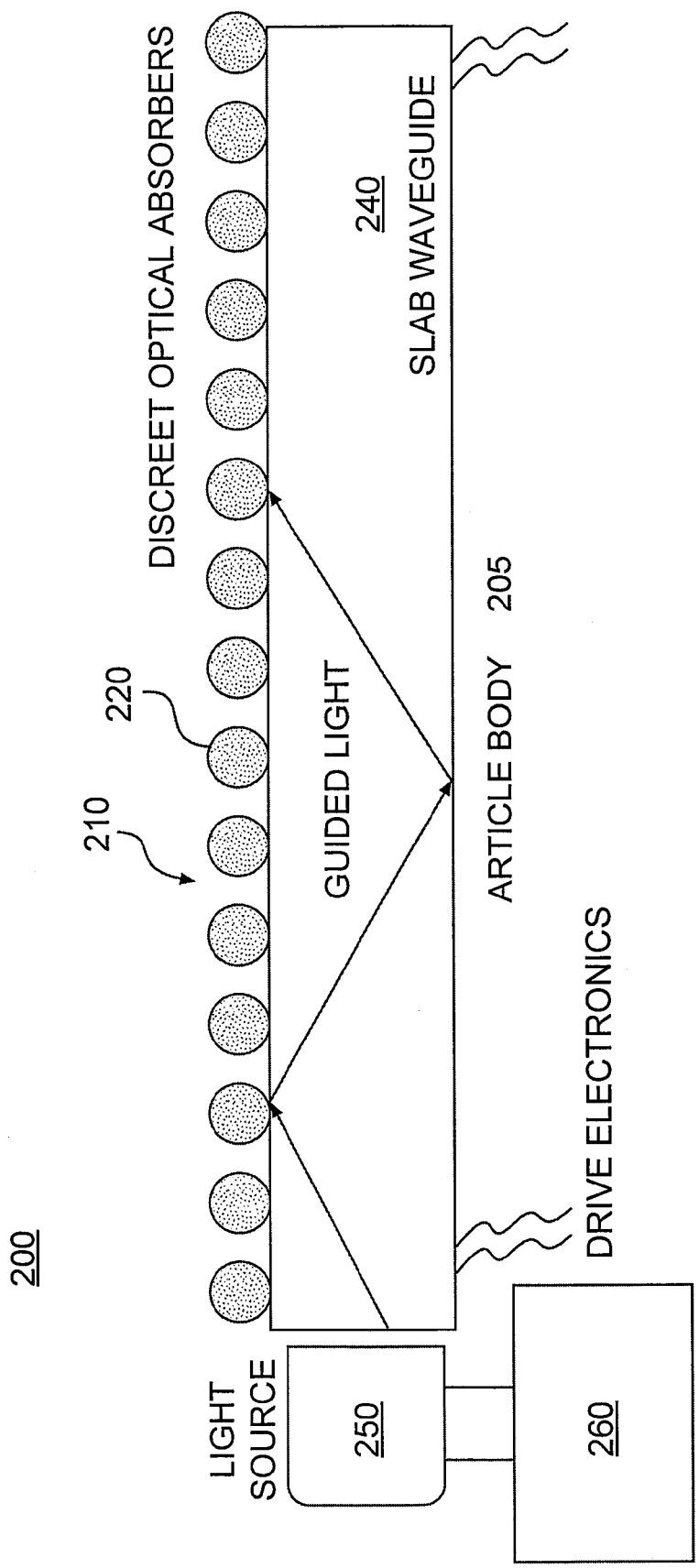
FIGS. 2A and 2B are schematic illustrations of an exemplary article having a contact surface that can be heat-sanitized to kill, impair or remove microbial growth, in accordance with the principles of the solutions described herein.
Figure 2B:
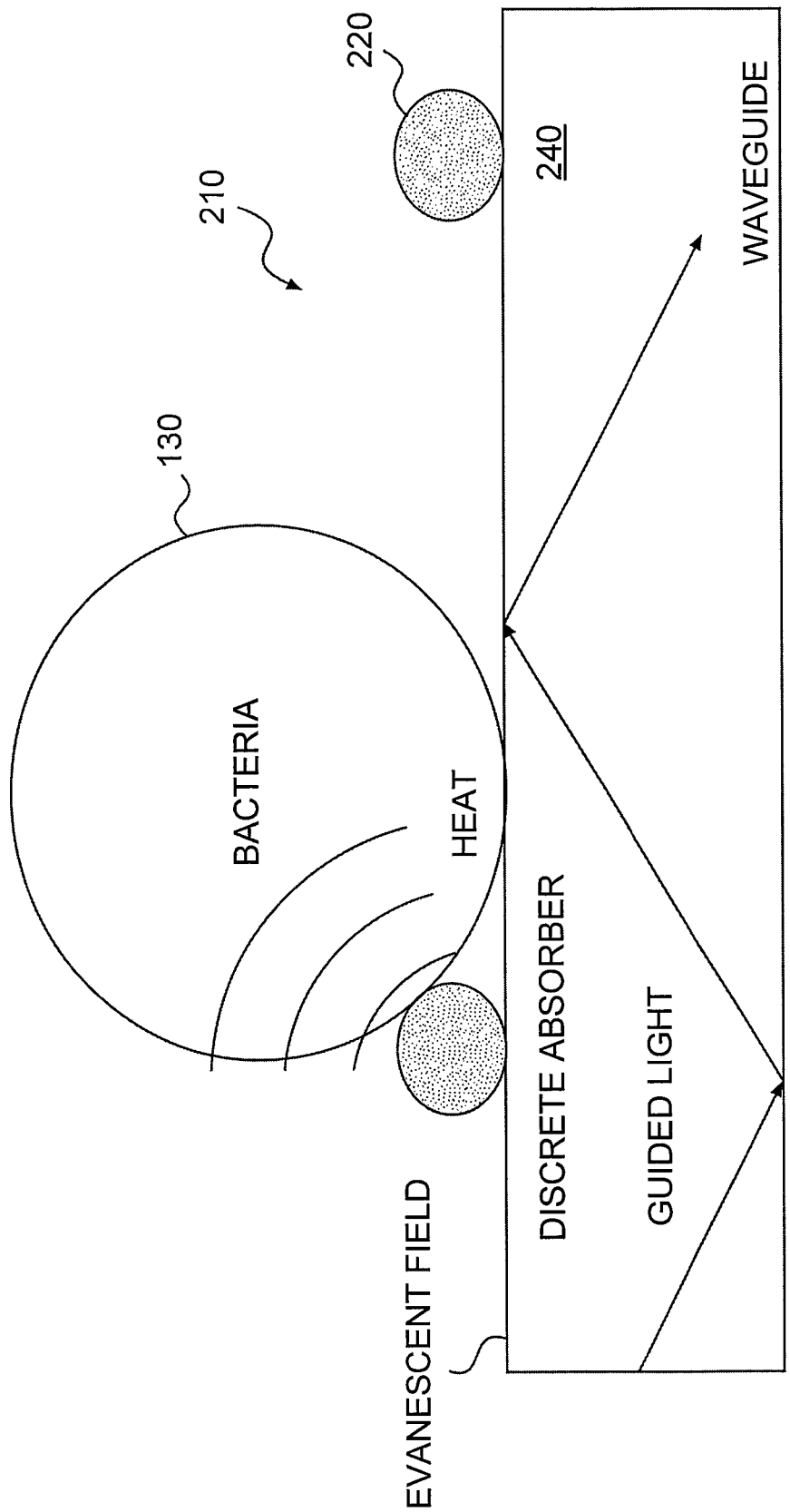

FIGS. 2A and 2B show an exemplary self-sanitizing article 200 having an article body 205 and an exterior surface 210, which includes a number of discrete heat-radiators (e.g., optical absorbers/re-radiators 220). Article 200 may be a device or fixture of any shape having one or more surfaces such as surface 210 that can be touched or contacted in use. Article 200 may, for example, be a computer or electronic display terminal, an electronic touch screen, a computer mouse or control device, a handle, a hand rail, a seat, a key board, a switch, a button, a knob, a computer mouse or control device, a desktop, a bathroom or kitchen or other working surface, a bus seat, a gymnasium apparatus or fixture, a restaurant booth or seat, a toy, a headphone, a telephone, an automatic teller machine, a vending machine, a shopping cart, a household device or fixture, a building device or fixture, an industrial device or fixture, a transport vehicle device or fixture, a medical device or fixture, or any other device or fixture whose contact surfaces are sites for potential transfer of undesirable pathogens amongst users.

Article 200 is configured so that outer surface region 210 can be periodically or continuously heat-sanitized by heat radiated by electromagnetic radiation absorber portions (e.g., discrete optical absorbers/re-radiators 220). Exterior contact surface 210, which includes optical absorbers/re-radiators 220, is disposed proximate to a electromagnetic radiation waveguide structure 240 (e.g., a slab waveguide), which is configured to guide selected electromagnetic radiation energy internally therethrough substantially parallel its outer surface region. Geometrically, the electromagnetic radiation waveguide structure 240 is interposed between article body 205 and exterior contact surface 210. Waveguide structure 240, may be made of any suitable material that is transparent to the selected electromagnetic radiation energy. Exemplary waveguide materials include glass, ceramic, plastics, polymers, quartz, CaF, Al2O3, Si3N4, and any combination thereof. Further in instances where the outer surface region 210 forms the exterior of an electronic display screen and/or an electronic touch screen or other visual device, waveguide structure 240 may be substantially transparent to a viewer of the underlying display.

Article 200 may include an internal source of electromagnetic radiation (e.g., light source 250) or be coupled to an external source that provides electromagnetic radiation energy for flow through electromagnetic radiation waveguide structure 240. The frequency of wavelength of the electromagnetic energy may be selected in conjunction with the design or structure of electromagnetic radiation waveguide structure 240 so that most if not all of the electromagnetic energy flow is in the lateral direction substantially parallel the waveguide's outer surface region. Source 250 may be configured to provide radiation of suitable wavelength and to inject such radiation into the waveguide structure. Source 250 may, for example, be an ultraviolet light source, an infrared light source, a short pulse laser, a LED and/or a flash bulb.

Suitable electronics (e.g., drive electronics 260) may be deployed to control operation of the source of electromagnetic radiation. Source 250 may be configured so that selected electromagnetic radiation propagating or flowing through waveguide structure 240 is in the form of short duration electromagnetic pulses. The pulses may have any suitable pulse width, for example, in the range of about nanoseconds to milliseconds.

In operation, the electromagnetic radiation absorber portions (220) are coupled to and heated by the electromagnetic radiation energy flow through the waveguide structure 240 to a positive temperature to heat-sanitize an exposed portion of exterior contact surface 210. Article 200 may be designed to have suitable positive temperature values for local heat sanitization. The suitable positive temperature values may, for example, be selected with consideration of the particular type of microorganisms that may expected on the surface and empirical knowledge of the critical temperatures required to kill or impair such microorganisms. The positive temperature values may be in the range of about 10° C. to 100° C. above ambient. In some versions of article 200, the suitable positive temperature values may exceed 100° C.

Figure 3A:
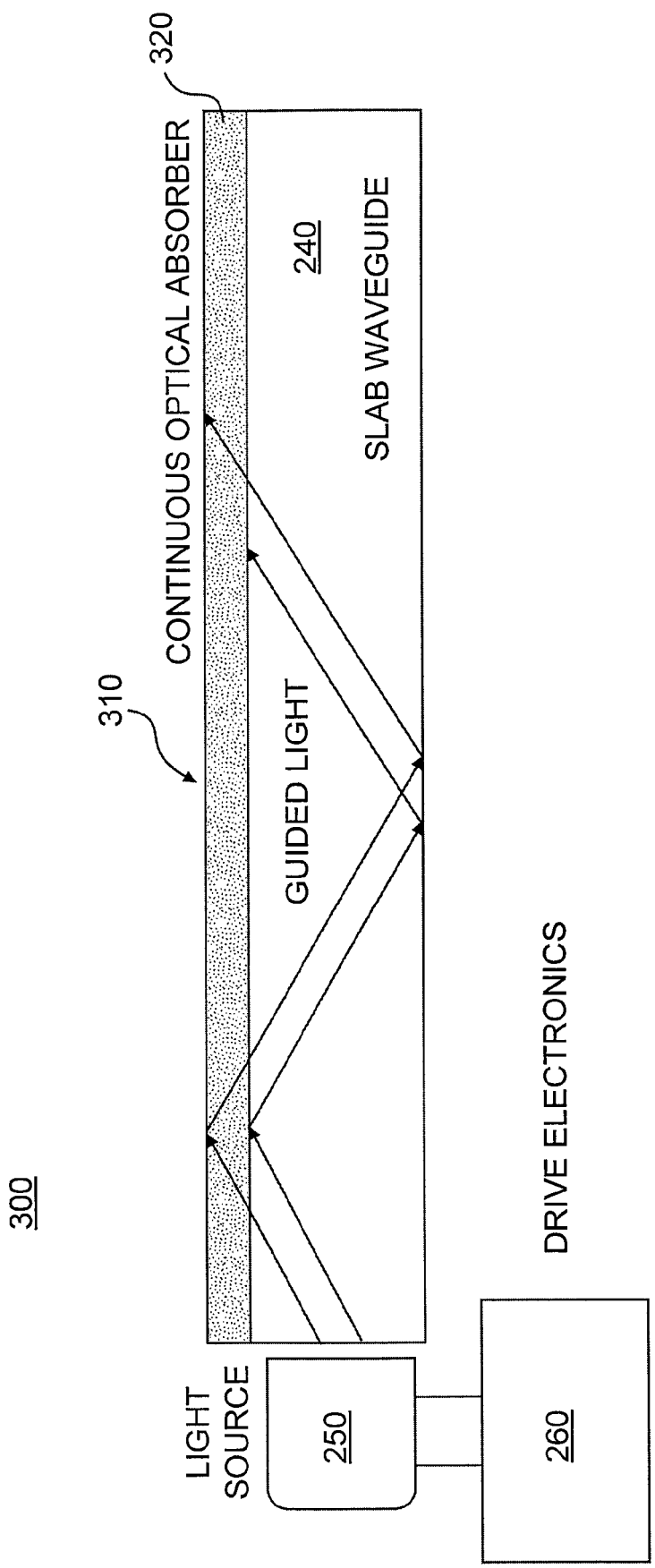
FIGS. 3A and 3B are schematic illustrations of another exemplary article having a contact surface that can be heat-sanitized to kill, impair or remove microbial growth, in accordance with the principles of the solutions described herein.
Figure 3B:
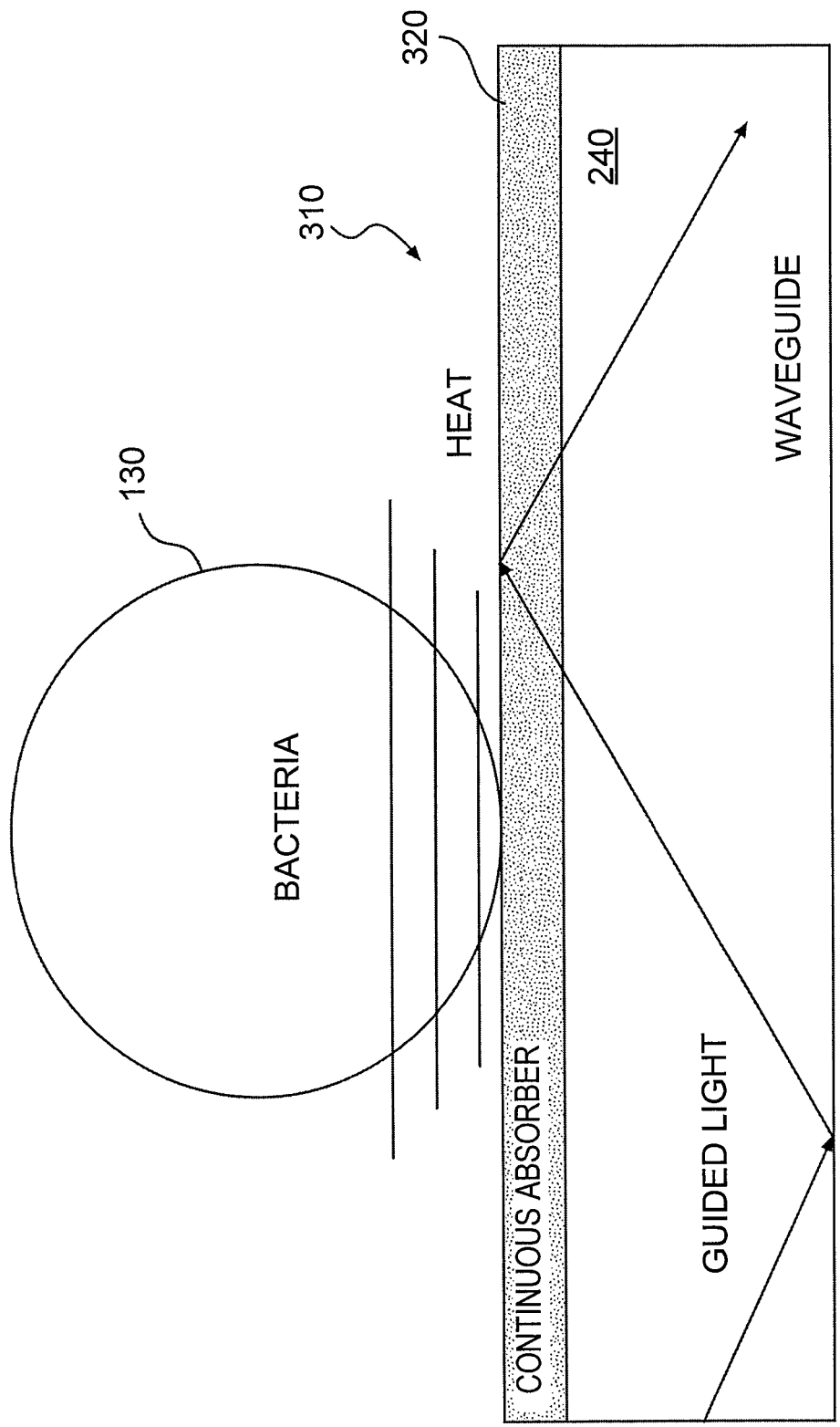

The electromagnetic radiation absorber portions 220 along a length of the waveguide structure may be coupled to and heated by an evanescent field component of the selected electromagnetic radiation energy flow through the waveguide structure. (See e.g., FIG. 2B). Alternatively or additionally, the waveguide structure may be configured to have multiple internal reflections of the electromagnetic radiation energy flow therethrough. The electromagnetic radiation absorber portions 220 may be coupled to and heated directly by portions of the electromagnetic radiation energy flow that undergo total internal reflection in the waveguide's exterior surface region 210. FIG. 3A shows an exemplary article 300 which has a structure similar to that of article 200, but in which the electromagnetic radiation absorber portion 320 is a substantially continuous adlayer which directly absorbs energy from electromagnetic radiation that undergoes reflection in surface region 310 of waveguide structure 240. The adsorbed energy is reradiated as heat to kill or impair microorganisms (e.g., bacteria 130) in the vicinity (FIG. 3B).

Electromagnetic radiation absorber portions 220 that are shown, for example, in FIGS. 2A and 2B, may include radiation-absorbing particles. These particles may be metallic particles that include one or more of gold, silver, aluminum, platinum, carbon nanotubes, and vanadium dioxide particles.

The particles may be nanoparticles that have suitably small dimensions (e.g., 20-200 nm) so that they exhibit size-dependent non-linear behavior. See e.g. John Kiran Anthony et al. "Particle size-dependent giant nonlinear absorption in nano-structured Ni—Ti alloys," Optics Express (2008) Volume: 16, Issue: 15, Pages: 11193-11202; Venkatram N. et al. "Size dependent multiphoton absorption and refraction of CdSe nanoparticles," Opt Express. 2007 Sep. 17; 15(19):12258-63; and Soumen Dhara et al. "Size-dependent visible absorption and fast photoluminescence decay dynamics from freestanding strained silicon nanocrystals," Nanoscale Res Lett. 2011 Apr. 11; 6(1):320.

The radiation-absorbing particles included in electromagnetic radiation absorber portions 220 may be nanoparticles that have sufficiently small dimensions so that they exhibit resonant coupling to and enhanced absorption of portions of the electromagnetic radiation energy flow in waveguide structure 240. The nanoparticles included in electromagnetic radiation absorber portions 220 may, for example, be gold nanoparticles having dimensions of about 20 nanometers which exhibit non-linear absorption of infrared radiation. An exemplary article 200 may have gold nanoparticles of about 20 nanometers as radiation absorbers 220 and an electromagnetic radiation energy flow through waveguide structure 240 of IR pulses having pulse widths of about 1 nanosec.

It will be understood that article 200 may include an arrangement of optical elements (not shown) that configured to direct the selected electromagnetic radiation energy generated by the radiation source into the waveguide structure.

Article 200 may further include a contact sensor configured to determine if a contact has been made to an exposed portion of the outer surface region and to accordingly activate radiation source 250 to provide the selected electromagnetic radiation energy to waveguide structure 240 for heat-sanitization of the exposed portion of the outer surface region 210. The contact sensor is any one of a capacitive, a resistive, a mechanical, a piezoelectric, a thermal, an ultrasonic, or an optical sensor.

Some versions of article 200 may include a programmable mechanism or controller configured to control activation of radiation source 250 to provide the selected electromagnetic radiation energy to the waveguide structure for heat-sanitization of an exposed portion of the outer surface region. The programmable mechanism or controller may control activation of the radiation source to provide the selected electromagnetic radiation energy to the waveguide structure for heat-sanitization of an exposed portion of the outer surface region according to a predetermined schedule. Alternatively or additionally, the controller may be configured to heat-sanitize the exposed portion of the outer surface region a predetermined time interval after a contact has been made. Article 200 may optionally include a user-activated switch configured to control activation of the radiation source to provide the selected electromagnetic radiation energy to the waveguide structure for heat-sanitization of an exposed portion of the outer surface region according to a user command. Article 200 may further optionally include a status indicator configured to indicate a sanitization state of the outer surface region.

FIG. 4 shows exemplary features of a method 400 for inhibiting germ transmission from contact surfaces. The method involves heat-sanitizing of an outer surface region of an article by heat-radiators included in the contact surfaces. Method 400 includes providing a selected electromagnetic radiation absorber portion in the outer surface region (410) and flowing selected electromagnetic radiation energy through an underlying waveguide structure substantially parallel to the outer surface region so that the selected electromagnetic radiation absorber portion is coupled to and heated by the electromagnetic radiation energy flow to a positive temperature that heat-sanitizes an exposed portion of the outer surface region (420). The positive temperature achieved by method 400 may be in the range of about 10° C. to 100° C. and higher above ambient as may be appropriate to provide effective heat sanitization.

In method 400, the selected electromagnetic radiation absorber portion may be a substantially continuous adlayer extending over a portion of the waveguide structure or may include discrete absorbers (e.g., radiation-absorbing particles) distributed over a portion of the waveguide structure. The radiation-absorbing particles may be nanoparticles having sufficiently small dimensions that allow resonant coupling to and enhanced absorption of portions of the electromagnetic radiation energy flow. In method 400, the selected electromagnetic radiation absorber portion may be coupled to and heated by an evanescent field component of the selected electromagnetic radiation energy flow through the waveguide structure. The selected electromagnetic radiation absorber portion may be coupled to and heated directly by portions of the electromagnetic radiation energy flow that undergo total internal reflection.

Further, in method 400 the selected electromagnetic radiation may include short duration electromagnetic pulses, for example, having pulse widths in the range of about nanoseconds to milliseconds.

Method 400 includes configuring a radiation source to provide the selected electromagnetic radiation energy to the waveguide structure. The radiation source so provided may be an ultraviolet light source, an infrared light source, a short pulse laser, a LED, and/or a flash bulb. Method 400 may optionally include providing an arrangement of optical elements to direct the selected electromagnetic radiation energy generated by the radiation source into the waveguide structure.

Method 400 may further include providing a contact sensor configured to determine if a contact has been made to an exposed portion of the outer surface region and to accordingly activate the radiation source to provide the selected electromagnetic radiation energy to the waveguide structure for heat-sanitization of the exposed portion of the outer surface region.

Method 400 may also include providing a programmable mechanism or other controller configured to control activation of the radiation source to provide the selected electromagnetic radiation energy to the waveguide structure for heat-sanitization of an exposed portion of the outer surface region. Method 400 may accordingly include using such programmable mechanism or other controller to provide the selected electromagnetic radiation energy to the waveguide structure for heat-sanitization of an exposed portion of the outer surface region according to a predetermined schedule, a predetermined time interval after a contact has been made and/or according to a user command.

Method 400 may further include providing a status indicator configured to indicate a sanitization state of the outer surface region.

All of the above U.S. patents, U.S. patent application publications, U.S. patent applications, foreign patents, foreign patent applications and non-patent publications referred to in this specification and/or listed in any Application Data Sheet are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:
1. A self-sanitizing article, comprising:
an electromagnetic radiation waveguide structure; and
an outer surface region disposed proximate to the electromagnetic radiation waveguide structure,
wherein the outer surface region has a selected electromagnetic radiation absorber portion and forms the exterior of at least one of an electronic display screen or an electronic touch screen,
wherein the electromagnetic radiation waveguide structure is configured to flow selected electromagnetic radiation energy internally therethrough substantially parallel to the outer surface region, and
wherein the selected electromagnetic radiation absorber portion is disposed relative to the waveguide structure so that it is coupled to and heated by the electromagnetic radiation energy flow to a positive temperature to heat-sanitize an exposed portion of the outer surface region.

2. The article of claim 1, wherein the waveguide structure is substantially transparent to a viewer of the at least one of the electronic display screen or the electronic touch screen.

3. A self-sanitizing article, comprising:
an electromagnetic radiation waveguide structure;
an outer surface region disposed proximate to the electromagnetic radiation waveguide structure; and
a status indicator configured to indicate a sanitization state of the outer surface region,
wherein the outer surface region has a selected electromagnetic radiation absorber portion,
wherein the electromagnetic radiation waveguide structure is configured to flow selected electromagnetic radiation energy internally therethrough substantially parallel to the outer surface region, and
wherein the selected electromagnetic radiation absorber portion is disposed relative to the waveguide structure so that it is coupled to and heated by the electromagnetic radiation energy flow to a positive temperature to heat-sanitize an exposed portion of the outer surface region.

4. A self-sanitizing article, comprising:
an electromagnetic radiation waveguide structure;
an outer surface region disposed proximate to the electromagnetic radiation waveguide structure,
wherein the outer surface region has a selected electromagnetic radiation absorber portion,
wherein the electromagnetic radiation waveguide structure is configured to flow selected electromagnetic radiation energy internally therethrough substantially parallel to the outer surface region, and
wherein the selected electromagnetic radiation absorber portion is disposed relative to the waveguide structure so that it is coupled to and heated by the electromagnetic radiation energy flow to a positive temperature to heat-sanitize an exposed portion of the outer surface region;
a radiation source configured to provide the selected electromagnetic radiation energy to the waveguide structure; and
a contact sensor configured to determine if a contact has been made to an exposed portion of the outer surface region and to accordingly activate the radiation source to provide the selected electromagnetic radiation energy to the waveguide structure for heat-sanitization of the exposed portion of the outer surface region.

5. The article of claim 4, wherein the selected electromagnetic radiation provided by the radiation source comprises short duration electromagnetic pulses.

6. The article of claim 4, wherein the selected electromagnetic radiation absorber portion is a substantially continuous adlayer extending over a portion of the waveguide structure.

7. The article of claim 4, wherein the selected electromagnetic radiation absorber portion includes discrete absorbers distributed over a portion of the waveguide structure, the discrete absorbers being physically separate from one another.

8. The article of claim 7, wherein discrete absorbers include radiation-absorbing particles.

9. The article of claim 8, wherein the radiation-absorbing particles are nanoparticles having sufficiently small dimensions that allow resonant coupling to and enhanced absorption of portions of the electromagnetic radiation energy flow.

10. The article of claim 4, wherein the radiation source is an infrared light source.

11. The article of claim 4, further comprising, a programmable mechanism configured to control activation of the radiation source to provide the selected electromagnetic radiation energy to the waveguide structure for heat-sanitization of an exposed portion of the outer surface region.

12. The article of claim 4, further comprising, a controller configured to control activation of the radiation source to provide the selected electromagnetic radiation energy to the waveguide structure for heat-sanitization of an exposed portion of the outer surface region according to a predetermined schedule.

13. The article of claim 4, further comprising, a user-activated switch configured to control activation of the radiation source to provide the selected electromagnetic radiation energy to the waveguide structure for heat-sanitization of an exposed portion of the outer surface region according to a user command.

14. The article of claim 4, wherein the outer surface region forms the exterior of at least one of an electronic display screen or an electronic touch screen.

15. The article of claim 14, wherein the waveguide structure is substantially transparent to a viewer of the at least one of the electronic display screen or the electronic touch screen.

16. The article of claim 4, further comprising, a status indicator configured to indicate a sanitization state of the outer surface region.

* * * * *